United States Patent
Yano

(10) Patent No.: US 11,293,912 B2
(45) Date of Patent: Apr. 5, 2022

(54) TOC MEASUREMENT METHOD AND TOC MEASUREMENT APPARATUS USED THEREFOR

(71) Applicant: ECOLO CO., LTD., Ibaraki (JP)

(72) Inventor: Kenkichi Yano, Ibaraki (JP)

(73) Assignee: ECOLO CO., LTD., Ibaraki (JP)

( * ) Notice: Subject to any disclaimer, the term of this patent is extended or adjusted under 35 U.S.C. 154(b) by 490 days.

(21) Appl. No.: 16/353,082

(22) Filed: Mar. 14, 2019

(65) Prior Publication Data

US 2019/0302085 A1 Oct. 3, 2019

(30) Foreign Application Priority Data

Mar. 30, 2018 (JP) .............................. JP2018-067105

(51) Int. Cl.
*G01N 33/18* (2006.01)
*G01N 31/00* (2006.01)

(52) U.S. Cl.
CPC ....... *G01N 33/1846* (2013.01); *G01N 31/005* (2013.01)

(58) Field of Classification Search
CPC .................... G01N 33/1846; G01N 31/005
See application file for complete search history.

(56) References Cited

U.S. PATENT DOCUMENTS 6,797,237 B2  9/2004 Morita et al.
2006/0053874 A1* 3/2006 Bauman ............. G01N 33/1846
73/114.75

FOREIGN PATENT DOCUMENTS

| CN | 103080683 | 5/2013 |
| JP | H08-068787 | 3/1996 |
| JP | 2003-075426 | 3/2003 |
| JP | 2011-220734 | 11/2011 |
| JP | 2013-096771 | 5/2013 |

* cited by examiner

*Primary Examiner* — Christopher Adam Hixson
(74) *Attorney, Agent, or Firm* — IPUSA, PLLC

(57) ABSTRACT

A method for measuring TOC in test water is disclosed. Test water is injected into a combustion tube, which is controlled to be heated in a state of flowing carrier air generated by discharging stored water filled in a combustion gas or carrier air storage tank. After the drying process, temperature in the combustion tube is increased, and the dried organic carbon is burned. Combustion gas is guided to the combustion gas storage tank. An inside of the combustion tube is purified due to high pressure steam generated by injecting pure water and organic carbon removed in the purification process is burned and oxidized. The generated combustion gas is guided to the combustion gas storage tank and is pushed into an infrared meter to measure a carbon dioxide gas concentration. Otherwise, the generated combustion gas is guided to the infrared meter to measure the carbon dioxide gas concentration.

7 Claims, 7 Drawing Sheets

TOC MEASUREMENT METHOD AND TOC MEASUREMENT APPARATUS USED THEREFOR

BACKGROUND OF THE INVENTION

The present invention relates to a method for measuring an amount of impurities contained in test water (also referred to as "sample water"), particularly the total organic carbon (hereinafter abbreviated as "TOC", and particularly relates to a method for efficiently cleaning an inside of a combustion tube during TOC measurement without requiring time or labor, and for precisely and highly accurately measuring TOC in test water, and a TOC measurement apparatus used for the method.

DESCRIPTION OF THE RELATED ART

Along with BOD (abbreviation for "biochemical oxygen demand") and COD (abbreviation for "chemical oxygen demand"), TOC is one of representative water quality indicators. TOC measurement is typically used and applied for management of pharmaceutical water (purified water, water for injection), water quality control of tap water, and management of factory wastewater, and items of TOC measurement are specified according to each use. However, in various sample water such as environmental water (rainwater, river water, groundwater, lake water, pond water, well water, and the like), washing water, domestic wastewater, industrial water, sewage water, cooling water, sea water, and the like, it has been desired to measure TOC more accurately, conveniently and cheaply.

As a TOC measurement method, a combustion oxidation method, a wet oxidation method, and a two-stage wet oxidation method are well known.

A UV wet oxidation method is a method, in which, after removal of inorganic carbon (hereinafter, abbreviated as "IC") from sample water, the TOC is oxidized (including use of an oxidizing agent) by UV irradiation to generate carbon dioxide, the generated carbon dioxide gas is conveyed to a carbon dioxide concentration detector by a carrier gas, and its concentration is measured (refer to Patent Document 1).

In a two-stage wet oxidation method, there are two stages in oxidizing organic carbon; a base oxidation phase using hydroxyl radicals as a first stage, and a TOC oxidation phase by ozone oxidation as a second stage. Features of the oxidation method are that oxidation with a relatively large capacity is realized, and oxidation of sample water containing salt can be performed because there is no damage to the reaction tube.

Contrary, as a first process (a measurement process of a total carbon amount), in a combustion oxidation method, basically, sample water is sent together with purified air or oxygen, from which $CO_2$ has been removed, to a combustion tube (usually using a quartz tube), which is filled with an oxidation catalyst (platinum, palladium, cobalt oxide or the like) and is heated to 900° C. through 950° C., and carbon content is oxidized to carbon dioxide; and its carbon dioxide is measured by infrared spectrometer or the like, so to determine a total carbon content. Next, IC measurement in the sample water is performed as a second process (IC removal process); that is, a certain amount of acid (oxidation catalyst such as hydrochloric acid, sulfuric acid, phosphoric acid, or the like) is added to the sample water, and it is sent to a heated combustion tube heated to approximately 150° C. and oxidized to carbon dioxide. Next, the carbon dioxide is measured with an infrared spectrometer or the like to obtain an IC amount. Next, as a third process (measurement process of TOC), the IC amount is subtracted from the total carbon amount to obtain a total organic carbon amount. It is a matter of course that the IC removing process can also be performed before the combustion oxidation process.

As a TOC measurement apparatus adopting such the combustion oxidation method, there is known the TOC measurement apparatus having a measurement section including an IC removal section from sample water, a sample water injection section after IC removal, a carrier gas supply section, a drip section, a combustion oxidation section equipped with a combustion tube filled with a catalyst and heated to 600° C. to 900° C., a $CO_2$ detector, and the like (refer to Patent Document 2).

Moreover, as a TOC analyzer particularly suitable for samples having a relatively large amount of moisture, a TOC meter has been developed. In the TOC meter, a cylindrical electric furnace for vaporizing water, which is set at a temperature (100° C. to 150° C.) at which moisture is vaporized, is disposed at a preceding stage to a high temperature combustion type electric furnace for combustion oxidizing a sample (a tube type electric furnace heated to 900° C. in which an oxidizing catalyst is disposed), and the temperature detector is provided at a rear stage of a combustion oxidizing furnace, the moisture in the sample is converted into water vapor in a moisture vaporizing furnace, passage of the steam is detected by a temperature detector, and then the sample is sent to the combustion oxidizing furnace. After the moisture in the sample is converted into water vapor in the moisture vaporizing furnace, passage of the water vapor is detected by the temperature detector, the sample is sent to the combustion oxidizing furnace. The combustion oxidizing furnace and the moisture evaporating furnace may be deployed with two separate furnaces arranged side by side. Alternatively, the combustion oxidizing furnace alone may be provided, and may be used as the moisture evaporating furnace by setting temperature inside the combustion oxidizing furnace to 100° C. to 150° C. in the preceding stage (refer to Patent Document 3).

The combustion oxidation method as described above relates to a TOC measurement apparatus, which may be referred to as a one-stage direct combustion method or a dry/combustion two-step method. In either TOC measurement apparatus, the oxidation catalyst is still necessary and it is inevitable to be expensive in terms of price.

Furthermore, as an innovative TOC measurement apparatus and TOC measurement method, the inventor of the present invention has developed what is referred to as "drying solidification/combustion method" for the first time. In general, a drying and combustion furnace is heated to 120° C. to 250° C., test water is introduced, and moisture is evaporated to be solidified. Thereafter, the inside of the furnace is heated to 650° C. to 850° C., $CO_2$ is generated from the dried and solidified organic matter, and the generated $CO_2$ is measured with an infrared analyzer (Non-Dispersive Infrared, NDIR). Referring to FIG. 5, the following TOC measurement apparatus and TOC measurement method are described below in detail.

The TOC measurement apparatus in the test water according to "dry solidification/combustion method" includes a combustion section formed by a combustion tube 115 concentrically containing a test water injection tube 107, and a combustion tube heating furnace having a structure, in which a main heater 108 is laid concentrically in the outside thereof. In a combustion tube input/output block 117 provided in a portion of the protruding combustion tube 115, which is not surrounded by the combustion tube heating furnace, a carrier air supply section for supplying test water 102 and/or carrier air 106 and a pure water supply section for supplying pure water 101 by a pure water pump 103, are provided so as to be switched and supplied to the test water injection tube 107 by a route switching valve 105. Also, the combustion tube input/output block 117 is provided with a combustion gas discharge port, a steam trap section for recovering the steam discharged from a combustion gas discharge port is connected and arranged, and is further connected to an infrared meter 114 for measuring combustion gas other than the steam discharged from the combustion gas discharge port. An apparatus having such a configuration is depicted as the TOC measurement apparatus in FIG. 5.

The TOC measurement method in the test water according to "dry solidification/combustion method" is a method including the following processes. In an injecting process, the test water 102, which is pumped by inspection pump 104, is injected into the combustion tube 115. In a generating process, the carrier air 106 is generated by discharging stored water filled in the combustion gas storage tank. In a drying process, the test water 102 is dried by heating the combustion tube 115 with the carrier air 106 flowing therethrough and by controlling temperature to 120° C. through 250° C. In a discharging process, steam generated in the heating process is discharged outside the pipe, the steam is cooled and removed by a cooling pipe 116. The removed steam is discharged to the drain 112.

Moreover, the following processes are conducted after completion of the drying process. In heating and burning processes, organic carbon, which is dried by increasing temperature inside the combustion tube 115 to 650° C. through 850° C., is heated and burned. In a cooling process, after the burning process is substantially finished and the temperature inside the combustion tube 115 is controlled to 650° C. through 850° C., the burning process is terminated and the combustion tube 115 is allowed to cool. After the generated combustion gas is sent to a gas cleaning tank 113 by a path switching valve 110, a measuring process is conducted to guide the combustion gas to the infrared meter 114 by the carrier air 106 to measure a carbon dioxide gas concentration of the combustion gas.

By this TOC measurement method, it is possible to inject the test water 102 in a large amount of 100 to 1000 times as much as the conventional test, in order to burn the dried and solidified organic matter, and is possible to measure the carbon dioxide gas concentration with high accuracy even at low concentration. Also, there are economic advantages. That is, because the generated $CO_2$ has a higher concentration, it is possible to use the infrared analyzer (NDIR) for detection, even with a low sensitivity. Moreover, because stainless steel may be used for the combustion tube, rather than expensive quartz, it is possible to maintain a price of an apparatus at very low. In addition to these advantages, because an auxiliary combustion tube 111 is provided, when volatile organic compounds having a low boiling point are generated in the drying process, it is possible to burning them again at this stage and to measure the carbon dioxide gas concentration (refers to Patent Document 4).

In the TOC meter of the dry solidification/combustion type described in Patent Document 4, because moisture in organic matters in test water evaporates is dried and the organic matters are burned, flammability is preferable and a detection rate reaches 92% or more; however, in a case of repeating the measurement many times, an undetected TOC component gradually adheres to a low temperature section of the combustion tube 115 and affects a next measurement. Therefore, there is a problem that it becomes impossible to perform correct measurement unless the undetectable organic carbon component adhering to the low temperature section is washed, removed, and cleaned. This problem is an inevitable task which causes more or less in all TOC measurement apparatuses employing the combustion oxidation method.

Therefore, conventionally, in order to make accurate measurements, after a general steam cleaning (steam at approximately 100° C.) is performed or disassembling and cleaning of the combustion tube 115 are performed every end of the measurement, the following measurement is performed. However, in general steam cleaning (steam at about 100° C.), washing and removal of the undetected TOC component adhered to the low temperature section has been inevitable and inadequate. Also, the disassembly and cleaning are not easily performed and requires time. For this reason, the above-mentioned TOC measurement apparatus is out of a purpose of a convenient continuous measurement.

PATENT DOCUMENTS

Patent Document 1: Japanese Laid-open Patent Publication No. 2003-075426
Patent Document 2: Japanese Laid-open Patent Publication No. 2011-220734
Patent Document 3: Japanese Laid-open Patent Publication No. H08-68787
Patent Document 4: Japanese Patent No. 5845056

SUMMARY OF THE INVENTION

According to an aspect of an embodiment, a method for measuring total organic carbon (TOC) in test water includes an injecting process that injects test water into a combustion tube; a drying process that controls the combustion tube to be 120° C. to 250° C. by heating the combustion tube in a state of flowing carrier air in accordance with a generation process that generates the carrier air by discharging stored water filled in a combustion gas storage tank or a carrier air storage tank, so that steam generated in the drying process is discharged outside the combustion tube to be cooled and removed; heating and burning processes, after completion of the drying process, that increase temperature in the combustion tube to be 650° C. to 850° C., and that heat and burn dried organic carbon, in which combustion gas is generated and guided to the combustion gas storage tank; a purification process that purifies an inside of the combustion tube due to high pressure steam generated by injecting pure water into the combustion tube with an extremely small amount at constant intervals at a plurality of times, when the burning process is substantially finished and temperature inside the combustion tube is controlled to be 650° C. to 850° C., wherein the burning process ends when organic carbon removed in the purification process is burned and oxidized; a cooling process that cools the combustion tube; and a measurement process that conducts either one of a first measurement manner and a second measurement manner, the first measurement manner guiding the generated combustion gas to the combustion gas storage tank by the carrier air and pushing out a total combustion gas stored in the combustion gas storage tank into an infrared meter so as to measure a carbon dioxide gas concentration of the combustion gas, the second measurement manner guiding the generated combustion gas to the infrared meter by the carrier air so as to measure the carbon dioxide gas concentration of the combustion gas.

According to another aspect of an embodiment, a method for measuring total organic carbon (TOC) in test water includes a process that forcibly peels off organic carbon scattered and adhered in a combustion tube by injecting pure water with a very small amount into the combustion tube at constant intervals at a plurality of times to generate high pressure steam, so as to purify the combustion tube, when a burning process during a TOC measurement is approximately finished and the temperature inside the combustion tube is controlled to be 650° C. to 850° C.

According to a still another aspect of an embodiment, an apparatus for measuring total organic carbon (TOC) includes a combustion section formed by a combustion tube concentrically containing a test water injection tube, and a combustion tube heating furnace having a structure, in which a main heater is laid concentrically on the outside of the combustion tube; a combustion tube input/output block provided in a protruding portion of the combustion tube, the protruding portion not being surrounded by the combustion tube heating furnace, in which a test water and/or carrier air supply section for supplying test water and/or carrier air and a pure water supply section for supplying pure water are provided so as to be supplied to the test water injection tube in a switchable manner, and a combustion gas discharge port is provided and a steam trap section for recovering steam discharged from the combustion gas discharge port is connected and deployed to the combustion gas discharge port; and an infrared meter that measures the combustion gas other than the steam discharged from the combustion gas discharge port, in which the steam trap section is connected to the infrared meter, wherein a gas storage section including a gas storage tank, which is laid between the steam trap section and the infrared meter or which is laid in front of a carrier air supply section for supplying the carrier air.

DETAILED DESCRIPTION OF THE PREFERRED EMBODIMENTS

In the following, embodiments of the present invention are described in detail with reference to the accompanying drawings.

In a total organic carbon (TOC) measurement apparatus, an accurate measurement may be performed by disassembling and cleaning a combustion tube at an end of each measurement and then conducting the next measurement; however, the disassembling and cleaning are not easily conducted and require time. Therefore, the inventor paid attention to a fact that it is only necessary to wash an inside of a combustion tube during the measurement, and has completed, as a result of trial and error repeatedly, the present invention.

For example, at a high temperature of combustion of 600° C. to 850° C., for example 800° C., when 0.3 ml to 0.5 ml, for example 0.5 ml, of pure water is introduced from a test water introduction pipe at one time, high temperature steam with the following capacity is instantaneously generated.

$$22400 \ cc \times (0.5/18) \times \{(800+273)/273\} = 2445 \ cc$$

Figure 1:
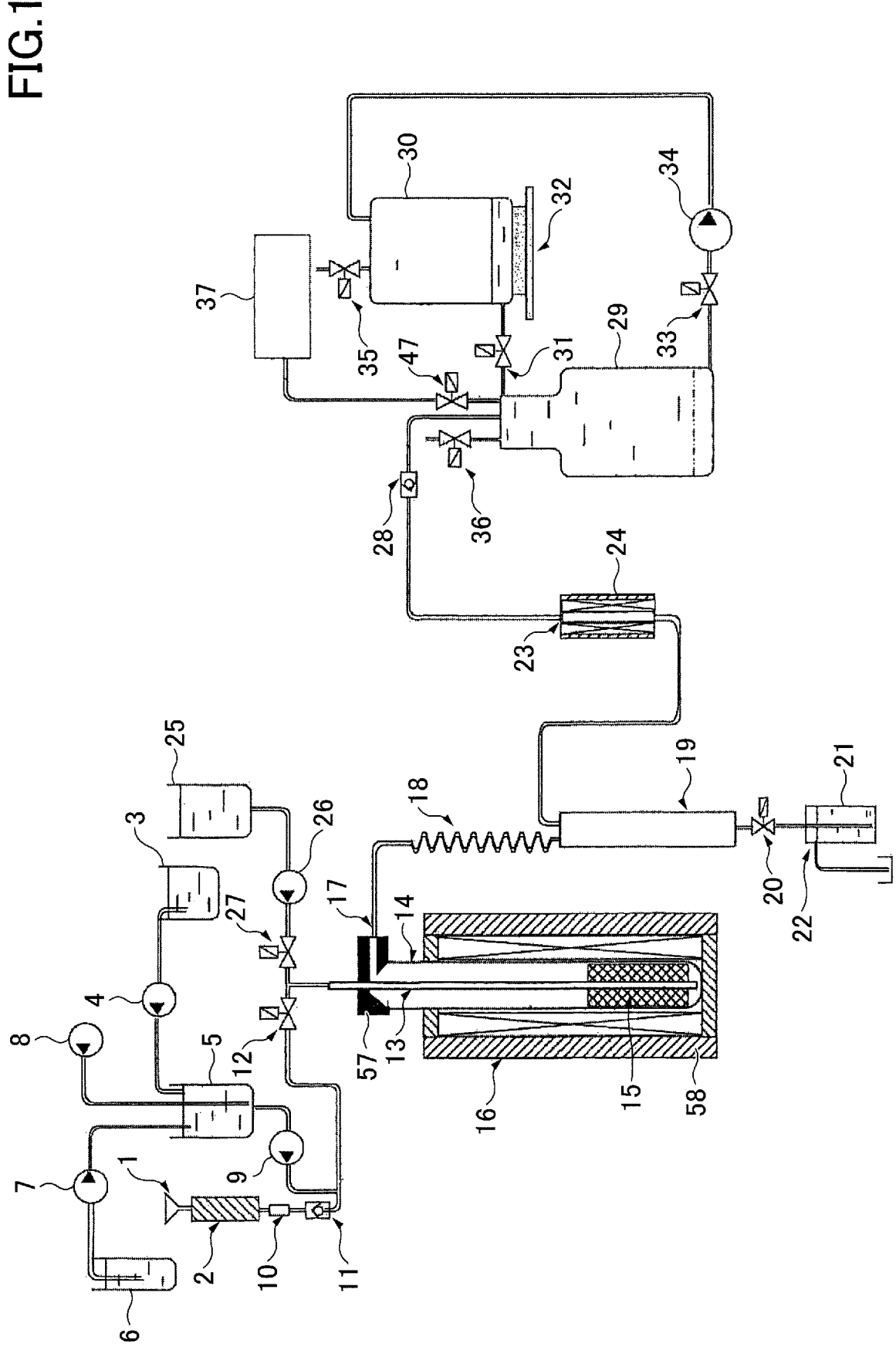
FIG. 1 is a diagram illustrating a configuration example of a TOC measurement apparatus of the present invention.

High-temperature steam at approximately 800° C. is exhausted more vigorously than a combustion gas discharge port (corresponding to an inspection water injection valve 12 in FIG. 1) while cleaning an inside of a combustion tube (corresponding to a combustion tube 14 in FIG. 1). By repeating this process for approximately 30 to 50 times every 5 to 10 seconds, unburned TOC component (small amount of 5% or less according to experiments) adhered to a low temperature section inside the combustion tube is forcibly peeled off and completely washed out. As disassembled and washed, adherents and combustion residues of TOC components disappear, and it is realized to eliminate a plus error of the measured value for the next measurement due to an influence of residual material contamination.

When the TOC component adheres to the low temperature section of the combustion tube during the measurement, the detection rate decreases correspondingly as a measurement result. In a case of discharging the TOC component without burning even if it is cleaned at high temperature during measurement, the detection rate is similarly lowered. Even if washing the combustion tube at high temperature after the end of the measurement, the detection rate decreases similarly. For this reason, in high temperature cleaning during the measurement, an amount of wash water introduced per time is reduced as much as possible, that is, 0.1 ml to 0.7 ml per time, preferably 0.1 ml to 0.5 ml per time, more preferably 0.1 ml to 0.3 ml per time, most preferably 0.1 ml to 0.2 ml per time to reduce an amount of generated steam, the TOC component mixed in the steam is made easy to be burned.

A number of washes is also increased from 5 to 80 times, preferably from 10 to 60 times, more preferably from 30 to 50 times at intervals of 5 to 20 seconds, preferably at intervals of 5 to 15 seconds, more preferably at intervals of 5 to 10 seconds. As a result, considerable $CO_2$ evolution was observed by burning attached organic carbon at low temperature (refer to FIG. 2). However, a flow rate of the combustion gas during this high-temperature cleaning is high at a time of introduction of pure water and immediately becomes an inversed rate, and a pulsation is intense and is not constant. Therefore, it is necessary to eliminate a measurement error due to carrier gas flow rate fluctuation at a time of occurrence of high-temperature steam during the measurement.

In a previous TOC measurement, a total amount of test water is burned with a constant carrier gas, and a TOC value of the test water is determined by converting into a theoretical value of $CO_2$ generation of a standard solution. Therefore, if a carrier gas flow rate is not constant, correct measurement cannot be performed.

In a conventional TOC meter, unless high temperature washing is performed for each measurement, contamination remains, and the next measured value becomes higher and incorrect.

For this reason, in a case of washing water is introduced at 0.5 ml per time×10 times at high temperature cleaning, a cleaning effect is quite high, but the detection rate is considerably low. In order to minimize the decrease in the detection rate as much as possible, the amount of wash water introduced per one time is reduced, and a number of times of washing is accordingly increased. For example, in a case of setting 0.3 ml per time×30 times, the detection rate becomes high. Even if the amount of washing water introduced is small or large, in a $CO_2$ measurement with an integral method assuming that the combustion gas passing through the infrared meter is constant, it is impossible to correctly measure with high temperature washing.

Therefore, a gas storage system of the present invention capable of accurate measurement even at the high temperature washing (refer to FIG. 1 and FIG. 2) is invented, so that in a method of introducing a total amount of combustion gas into a gas storage tank, carrying out a $CO_2$ measurement in the gas storage tank, obtaining a total $CO_2$ amount from a capacity of the gas storage tank, and converting the total $CO_2$ amount into a TOC value of the test water, measurement with high precision is made for a first time. In the gas storage system (refer to FIG. 1 and FIG. 2) of the present invention, a gas storage tank can be installed at an arbitrary measurement site. An aspect is recommended from a viewpoint of an operation, such that a gas reservoir including the gas storage tank is deployed between a steam trap section and the infrared meter, or is deployed in front of a carrier air supply section for supplying carrier air. In this system, a flow meter, a regulator, and a compressor are not necessary because the carrier gas flow rate is determined by a suction force of a stored liquid discharge pump at a bottom of the gas storage tank.

The present invention does not require to perform an insufficient steam cleaning (steam at approximately 100° C.) at an end of each measurement or to disassemble and clean a combustion tube, which are conventionally conducted, in a TOC measurement apparatus for measuring TOC contained in test water by a dry solidification/combustion method. The present invention particularly relates to a method for measuring TOC, in which enables accurate and highly precise TOC measurement by efficiently cleaning the inside of a combustion tube without hands, and provides a TOC measurement apparatus used for the same.

In the following, a TOC measurement apparatus of the present invention will be described with reference to FIG. 1, however the present invention is not limited thereto.

The TOC measurement apparatus of the present invention includes a combustion tube 14 concentrically containing a water injection tube 13, and a combustion section having a structure, in which a main heater 58 is laid concentrically on an outside of the combustion tube 14. On one side of the combustion tube 14, a test water and/or carrier air supply for supplying test water and/or carrier air, and a pure water supply part for supplying deionized water are arranged so as to be supplied in a switchable manner to the test water injection tube 13. On the other side of the combustion tube 14, a steam trap section for recovering a steam discharged from a combustion gas discharge port 17 is provided. Moreover, in the TOC measurement apparatus having a structure, in which it is connected to an infrared meter 37 for measuring combustion gas other than steam discharged from the combustion gas discharge port 17, a gas storage section including a combustion gas storage tank 29 is laid between the steam trap section and the infrared meter 37.

In the TOC measurement apparatus of the present invention, a method for providing a most characteristic gas reservoir is a method that eliminates a measurement error due to fluctuation of a carrier gas flow rate at a time of washing with high temperature steam during measurement, and is called "combustion gas storage method".

In FIG. 1, in the gas storage section, reservoir (water) filled in the combustion gas storage tank 29 is transferred from a reservoir discharge pipe provided at a lower part of the combustion gas storage tank 29 to an upper part of an auxiliary storage tank 30 via a reservoir discharge valve 33 and a reservoir discharge pump 34. The reservoir is supplied from the reservoir supply pipe, which is provided at the lower part of the auxiliary storage tank 30, to the upper part of the combustion gas storage tank 29 via a reservoir supply valve 31. An electronic scale 32 is provided at a bottom of the auxiliary storage tank 30, and increment and decrement of the transported reservoir are recorded every moment.

For example, during the measurement, in a case in which an injection amount of 0.1 ml per time×60 times is performed every 5 seconds, a cleaning time is 300 seconds (5 minutes). Meanwhile, a carrier gas, which is essential for the measurement, cannot be stabilized and becomes a pulsating state, and an error occurs in a measurement for obtaining an indicator value concentration of the infrared meter 37 by an areal reserves prediction method under a constant carrier gas. For this reason, as a result of ingenuity devised for a purpose of eliminating such measurement error due to fluctuation of the carrier gas flow rate, this "combustion gas or carrier gas storage method" is reached.

A conventional gas regulator is weak against dirt and quickly become malfunctioning, and also is expensive. An operation of a conventional flow meter also becomes unstable due to dust and dirt, and the flow meter erroneously displays. With regular meter, it is impossible to display and control momentary flow rate. An expensive meter can display and control with a flow meter position sensor or the like, however, the meter has large errors.

On the contrary, in a case of carrying out the measurement with "combustion gas or carrier gas storage method" of the present invention, because a gas path is not an extremely thin tube like a gas regulator or a flow meter, an inner diameter on the gas path is 4 mm to 5 mm as a usual pipe. Hence, it is possible to stably record with strong resistant to dirt and dust. Moreover, it is possible to manage a successive change of the carrier gas flow rate, and by controlling the reservoir discharge pump 34 according to an output of the reservoir, it is possible to maintain a flow constant.

By using the TOC measurement apparatus of the present invention provided with the storage section, regardless of an amount of pure water introduced, that is, regardless of an amount of generated steam, it becomes possible to easily realize accurate and highly precise measurement without requiring a special advanced measurement skill.

Moreover, the TOC measurement apparatus of the present invention is provided with an auxiliary combustion section from the steam trap section to a gas storage section. By this structure, an incomplete combustion gas and the like generated in a burning process are completely burned in the auxiliary combustion section, so as to realize a more accurate measurement.

A test water supply section is formed by a test water tank 3, an inspection pump 4, and a test water metering injection pump 9, and supplies a certain amount of the test water to the combustion tube 14 via the inspection water injection valve 12 and a water injection tube 13.

In a case of removing an IC component in the test water beforehand, an IC removing section is provided between the test water tank 3 and the test water metering injection pump 9.

The IC removing section includes an inorganic carbon removal tank 5 that stores the test water being conveyed from the test water tank 3 by the inspection pump 4 and that removes IC components from the test water, a hydrochloric acid tank 6 that stores the test water in order to supply, by a hydrochloric acid injection pump 7, acid for acidifying the test water, for example, hydrochloric acid, to the inorganic carbon removal tank 5, and an aeration air pump 8 that removes $CO_2$ in the inorganic carbon removal tank 5. The IC removing section functions to remove the IC component in the test water as carbon dioxide gas.

A carrier gas supply section includes an air inlet 1, a $CO_2$ absorption tank 2 that absorbs and removes $CO_2$ from the air, a flow meter 10, and a check valve 11. The carrier gas, which is supplied from the carrier gas supply section, supplies oxygen necessary for combustion oxidation, transfers a $CO_2$ gas generated by combustion to a measurement section, and cleans an inside of the TOC measurement apparatus and a gas flow path.

A pure water (also called "washing water") supply section includes a washing water tank 25, and a washing water injection pump 26. The washing water is supplied to the combustion tube 14 by the washing water injection pump 26 through a washing water injection valve 27 and the water injection tube 13.

A combustion section includes the combustion tube (made of stainless steel 304) that concentrically stores a bumping prevention material for preventing bumping and scattering, for example, metal gauzes 15 or the like on the test water injection tube 13 and outside thereof, and a combustion tube heating furnace 16 that has a structure, in which the main heater 58 is also laid concentrically on the outside of the combustion tube 14, and is heated to 600° C. through 850° C. Considering heat-resistant corrosion resistance, the combustion tube is made of stainless steel. The combustion tube is preferably usually 30 mm in any range of an inner diameter of 20 mm to 60 mm, and is preferably usually 15 cm to 30 cm in any range of 10 cm to 40 cm in height.

A carrier air supply section for supplying the test water and/or the carrier air and a pure water supply section for supplying the pure water are connected in the combustion tube input/output block provided in a protruding combustion tube portion, which is not surrounded by the combustion tube heating furnace 16, so that the carrier air supply portion and the pure water supply portion are selectively supplied to the test water injection tube 13. Also, the combustion gas discharge port 17 is provided, and a steam trap section for recovering the steam discharged from the combustion gas discharge port 17 is connected and provided.

The steam trapping section is a device part for recovering the steam discharged from the combustion gas discharge port 17, and includes a cooling pipe 18, a buffer tank 19, a drain discharge valve 20, a drain cup 21, an overflow discharge pipe 22, and the like.

Next, combustion gas other than the steam discharged from the combustion gas discharge port 17 passes through the steam trap section and is guided to the storage section via an auxiliary combustion tube 23 and the check valve 28.

The storage section is designed so that the combustion gas is stored in the combustion gas reservoir 29, by transferring the reservoir in the combustion gas storage tank 29 to the auxiliary storage tank 30 by the reservoir discharge pump 34 through the reservoir discharge valve 33 provided at a lateral lower part of the combustion gas storage tank 29. The capacity of the combustion gas storage tank 29 is usually 6 L in any range of 4 L to 12 L. The combustion gas storage tank 29 is usually shaped in a pipe, and an inner diameter thereof may be usually 10 cm in a range of 5 to 30 cm. The height of the combustion gas storage tank 29 may be set arbitrarily, however, in consideration of the measurement scale, a range of 50 cm to 120 cm may be suitably used, and a range of 80 to 120 cm may be preferably used.

In addition, the storage section includes a check valve 28, a discharge valve 36, the electronic scale 32, an intake valve 35, the auxiliary storage tank 30, a reservoir supply valve 31, and the like.

The combustion gas storage tank 29 is connected to the infrared meter 37 via an infrared measuring gas injection valve 47. The total combustion gas stored in the combustion gas storage tank 29 is extruded to the infrared meter 37, and a $CO_2$ concentration of the combustion gas is measured.

For a flow path for taking out, supplying, or distributing the test water (also called "pure water"), the washing water, the reservoir, the carrier air (also referred to as "carrier gas"), the combustion gas, or the like, a conventional pipe or hose is used. Normally, materials to be used are adjusted in consideration of heat, temperature, or the like of the device part. A heat resistant metal pipe such as stainless steel or aluminum, a hose made of thermoplastic resin such as polyester, polyethylene or heat resistant resin, a pipe may be used. A hose or pipe diameter (inner diameter) of about 0.3 mm to 8.0 mm may suitably be used.

In the following, a measurement procedure using the "(combustion) gas storage system" in FIG. 1 will be described.

Before a Start of the Measurement

The temperature of the combustion tube 14, 120° C. or less.

The combustion gas storage tank 29 is full water and a weight (W1) is measured.

1. The temperature of the combustion tube 14 is set at 600° C.
2. the test water of 100 ml in the test water tank 3 is injected into the inorganic carbon removal tank 5 by the inspection pump 4.
3. 2 mol hydrochloric acid of 1 ml is injected into the inorganic carbon removal tank 5 by a hydrochloric acid injection pump 7.
4. Aeration is performed in the inorganic carbon removal tank 5 for 90 seconds by the aeration air pump 8.
5. After removal of the inorganic carbon, the test water of S ml is injected into the combustion tube 14 by the test water metering injection pump 9.
6. The combustion tube 14 rises to a drying temperature of 250° C.
7. Operate the reservoir discharge pump 34 at 100 ml/min.
   Confirm the carrier gas approximately 100 cc/in with the flow meter 10.
   A water level drops in the combustion gas storage tank 29.
8. The temperature of the combustion tube 14 rises to 600° C.
9. Start washing the combustion tube 14 at 50 minutes after a start of the measurement (0.1 ml/time 60 times at 5 second intervals, and 5 minutes washing).
10. The measurement is terminated and the temperature of the combustion tube 14 is maintained at 600° C. for 2 minutes.
    An operation of reservoir discharge pump 34 is stopped.
11. Measure a weigh (W2) of the combustion gas storage tank 29.
12. Perform a high-temperature steam cleaning after completion of the measurement.
    At 5 minutes intervals, water injection at 0.4 ml/min 20 times (washing for 100 seconds).
13. The temperature of the combustion tube 14 is dropped.
14. Put water into the combustion gas storage tank 29 from the auxiliary storage tank 30 to be full water. At this time, the carbon dioxide gas concentration discharged from the combustion gas storage tank 29 is measured by the infrared meter 37.

15. The TOC value of the test water is:

$$Y = (x \times (W1 - W2) \times 18)/(S \times 22400).$$

(Y denotes a TOC concentration [mg/l], x denotes a carbon dioxide concentration [ppm], W denotes a weight [g], and S denotes a volume [ml].)

A method for measuring the $CO_2$ concentration in the present invention is a method using the infrared meter 37, which the carbon dioxide is measured when discharged from the combustion gas storage tank 29 and the amount of the carrier gas introduced into the combustion gas storage tank 29. Therefore, a fluctuation of the carrier gas flow during the measurement does not cause an error to a measured value.

Figure 2:
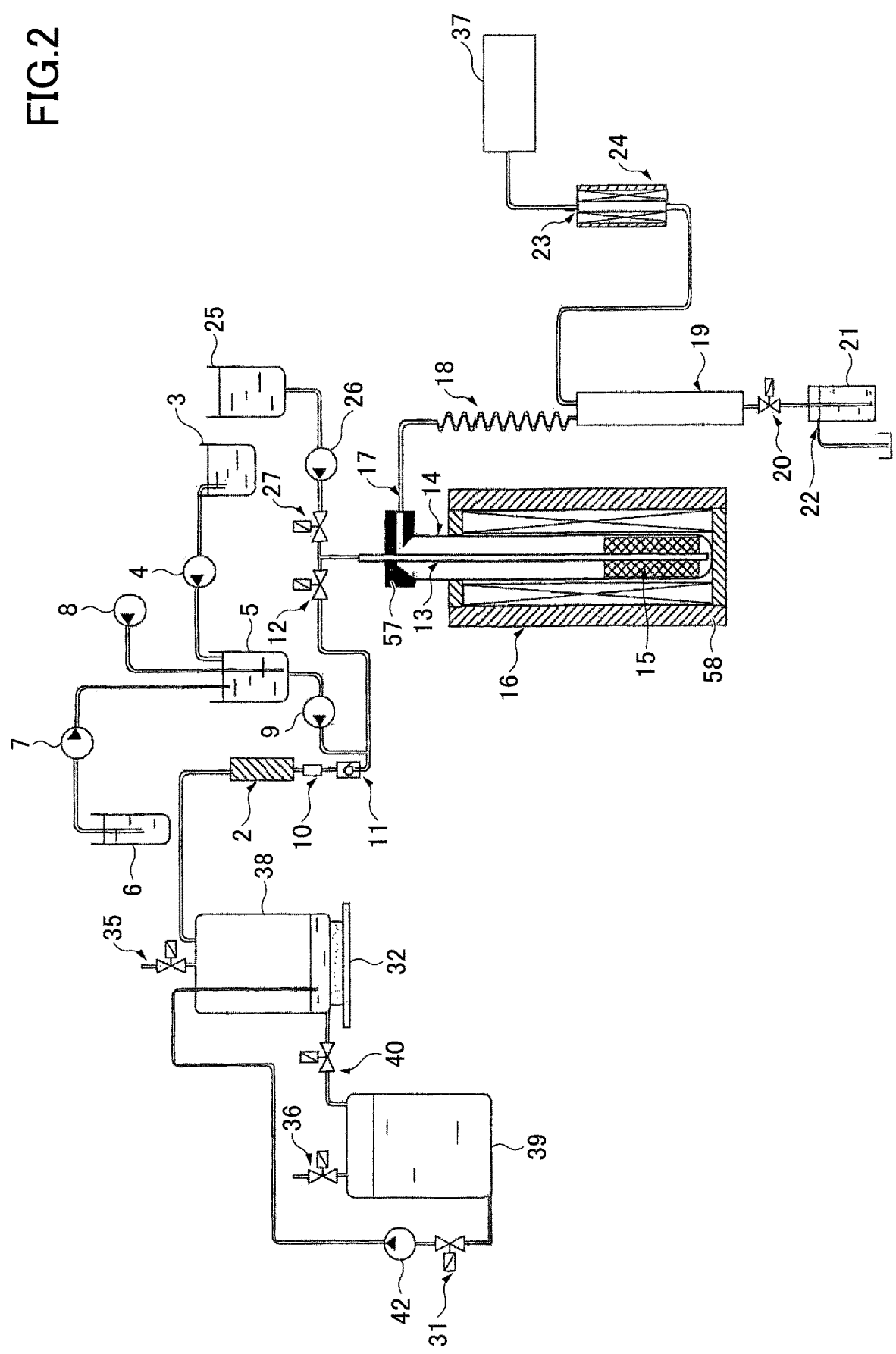
FIG. 2 is a diagram illustrating another configuration example of the TOC measurement apparatus of the present invention.

A measurement operation flow in the TOC measurement apparatus of the present invention has been described with reference to FIG. 1. The TOC measurement apparatus depicted in FIG. 1 is one aspect (referred to as "combustion gas storage method") of a "gas (combustion gas or carrier gas) storage method", which is carried out by installing the gas storage section immediately before the infrared meter 37. The present invention is not limited to this aspect. As another aspect, as depicted in FIG. 2, by connecting and installing the gas storage section immediately before the $CO_2$ absorption tank 2 (this is regarded as one mode of "gas (combustion gas or carrier gas) storage method" and is referred to as "carrier gas storage method"), the carrier gas can be stably generated and supplied from the gas storage section and a process can be similarly carried out.

1. Carrier Air Generation Process
(1) Measure the weight (W1) when the carrier air is full.
(2) Open the intake valve 35. Stored water (for example, water) in the carrier air storage tank 38, which is filled up to a top in advance with the reservoir, for example, tap water, is discharged by opening a reservoir discharge valve 40 and is stored in an auxiliary carrier air storage tank 39. By this operation, the carrier air due to retraction is generated inside the gas storage tank.

2. Test Water Injection Process for Injecting to Combustion Tube
(1) Open the inspection water injection valve 12, and connect a flow path of the test water metering injection pump 9 to the combustion tube 14 via a combustion tube input/output block 57 and the water injection tube 13.
(2) Turn ON the test water metering injection pump 9 for a specified period of time, and inject a specified amount of the test water into the combustion tube 14. After injecting the specified amount, the test water metering injection pump 9 is also closed.

3. Drying Process of Test Water in Combustion Tube
(1) Open the inspection water injection valve 12, and turn ON the combustion tube heating furnace 16 in a state of running carrier air by turning ON a reservoir supply pump 42, so as to heat the combustion tube 14. The heating temperature is controlled to 150° C. through 250° C., which is lower than the combustion temperature.
(2) In order to prevent a heating area expansion, bumping, and scattering of the test water in the drying process, a wire mesh, or the like is installed in the combustion tube 14.
(3) The steam generated by heating the combustion tube 14 is discharged to the outside of the combustion tube 14 via the combustion tube input/output block 57 with internal steam pressure, carrier air, and the like.

The discharged steam is cooled by the cooling pipe 18 through the combustion gas discharge port 17 and guided to the buffer tank 19, and dewing water in the buffer tank 19 is discharged from the drain discharge valve 20 after the measurement is completed.

(4) Residual dewing water is led to the combustion gas storage tank 29 via the auxiliary combustion tube 23.

An incomplete combustion gas and the like are completely burned in the auxiliary combustion tube 23 due to a temperature deviation of a furnace wall generated in the drying process.

4. Burning Process
(1) After completion of the drying for the specified time, a main heater 58 is controlled to raise the temperature of the combustion tube 14 to 650° C. through 850° C.
(2) Corresponding to the rising temperature, dry organic matters in the combustion tube 14 are burned and generates combustion gas.

The combustion gas is guided to an infrared meter 37 via the buffer tank 19 and the auxiliary combustion tube 23 in the same process as the drying process by the carrier air.

Incomplete combustion gas and the like are completely burned in the auxiliary combustion tube 23 due to the temperature deviation of the furnace wall generated in the burning process and the like.

5. Cleaning During Measurement (Also Referred to as "High Temperature Steam Cleaning") Process
(1) At a latter half of the burning process, when the combustion is almost finished, a pure water injection pump (for example, an injection pump for 30 ml/min) is driven for inching (0.1 to 0.6 seconds, preferably 0.1 to 0.4 seconds, more preferably 0.2 to 0.3 seconds) at regular intervals, a specified number of times (5 to 80 times, preferably 10 to 60 times), and the pure water is injected into the combustion tube 14 with extremely small amounts (0.05 to 0.3 ml/time, preferably 0.05 to 0.2 ml/time, more preferably 0.1 to 0.15 ml/time).

Even if cleaning high-temperature steam during measurement, in order not to lower a combustion recovery rate of the TOC component, the amount of wash water per one time is reduced and a number of washing is increased. As the amount of washing water per one time of the high temperature steam to such an extent that the unburned matter adhered to the low temperature portion of the combustion tube 14 is washed off into a high temperature combustion tube, 489 cc of steam for the washing water of 0.1 g is generated. That is, $$0.1 \text{ g}/18 \text{ g} \times 22{,}400 \times (800 + 273° \text{ C.})/273° \text{ C.} = 489 \text{ cc.}$$

(2) By the above process (1), the high pressure steam is generated in the combustion tube 14, the organic matter scattered and adhered in the combustion tube 14 is forcibly peeled off and burned by the steam, and the generated combustion gas is measured and recorded by an infrared meter 37 in the same manner as a normal combustion. Therefore, it is possible to realize more accurate measurement (a recovery ratio 95% with respect to a theoretical value of $CO_2$ generation is confirmed).

6. Measure the Weight (W2) of a Carrier Gas Stored Tank.

7. Cleaning-after-Measurement (Also Referred to as "High Temperature Steam Cleaning after Completion of Measurement") Process
(1) In order to reduce a thermal stress load of the combustion tube 14 after the completion of the combustion, when the temperature of the combustion tube 14 drops to a constant temperature (350° C. to 650° C.), the pure water injection pump is driven for inching (0.2 to 2.0 seconds, preferably 0.4 to 1.8 seconds, more preferably 0.6 to 1.6 seconds) at regular intervals (5 to 15 seconds, preferably 5 to 10 seconds), for a specified number of times (10 to 60 times, preferably 20 to 50 times, more preferably 20 to 30 times), and the pure water is injected into the combustion tube 14 at a rate of 0.1 to 1.0 ml/time, preferably 0.2 to 0.9 ml/time, more preferably 0.3 to 0.8 ml/times.

(2) By the above process (1), it is possible to further clean the inside of the combustion tube 14 and to prevent contamination. It is possible to minimize an influence due to the contamination at a time of a next measurement and before the measurement, and to enable a continuous measurement with high accuracy.

8. Combustion Gas Concentration Measurement Process (1) The temperature of the combustion tube 14 drops.

(2) The combustion gas discharged from the combustion gas discharge port 17 is continuously measured by the infrared meter 37 from the start of the measurement.

Figure 3:
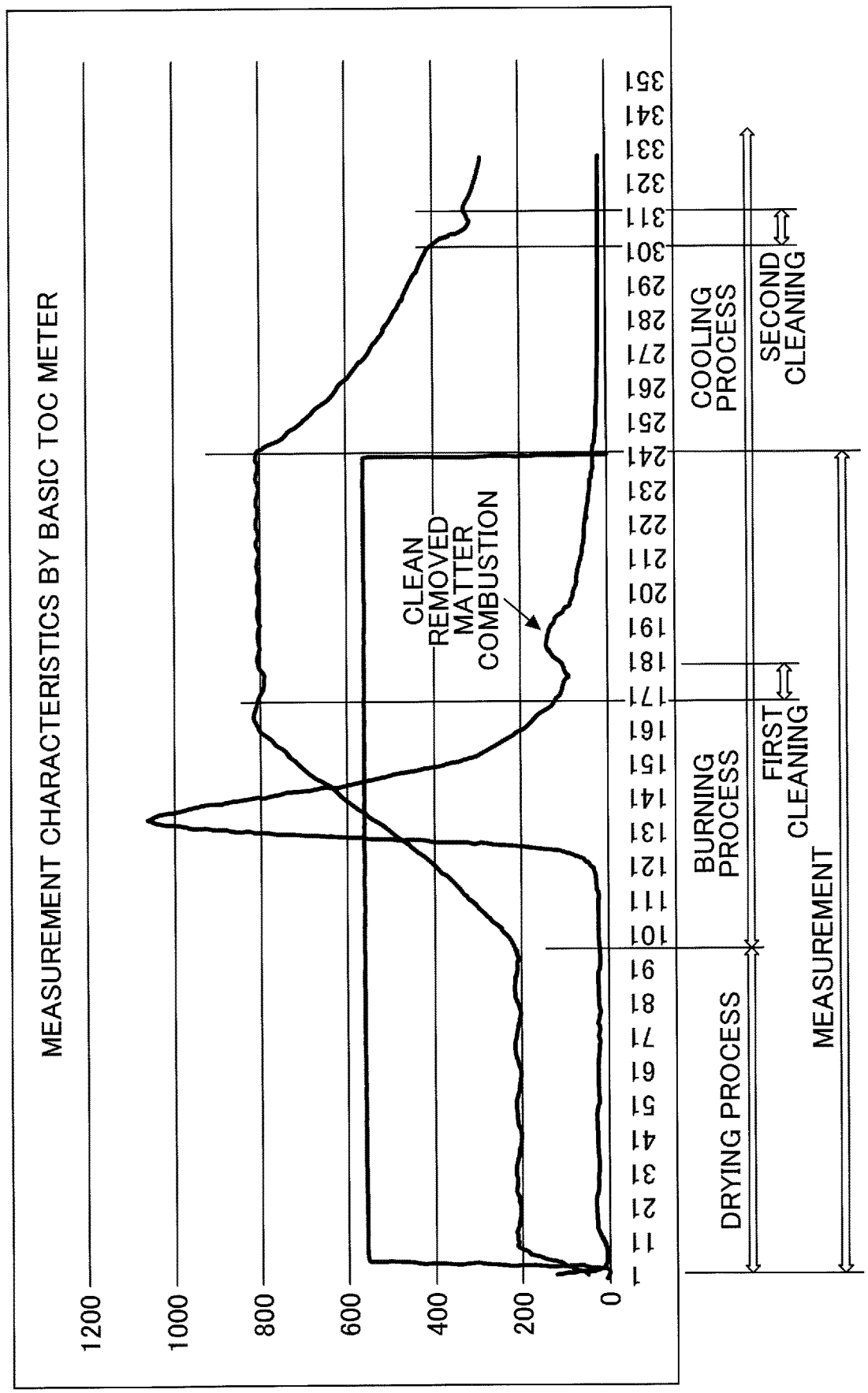
FIG. 3 is a diagram illustrating measurement characteristics by the TOC meter of the present invention.

In the above described operation flow of a basic TOC meter with a cleaning function, "cleaning process during measurement" is an indispensable cleaning process in order to achieve an accurate and more precise measurement (the recovery rate 95% or more against the theoretical value of the $CO_2$ generation). Referring to FIG. 3 illustrating a "measurement characteristics by basic TOC meter" of the present invention in a graph, this is apparent from the fact that small protrusions of measurement characteristics due to "cleaned and removed matter combustion" appear immediately after a first cleaning process (which is "cleaning process during measurement").

On the contrary, a "post-measurement cleaning process" is additionally carried out in the cleaning process during the measurement to further clean the inside of the combustion tube 14, in order to realize the high accurate continuous measurement; therefore, this process is not an essential cleaning process. Accordingly, the "post-measurement cleaning process" may be omitted, and there is no inconvenience at all. Referring to FIG. 3 illustrating the "measurement characteristics by basic TOC meter" of the present invention in the graph, this is apparent from the fact that there is no change in the measurement characteristics immediately after a second cleaning process ("post-measurement cleaning process").

Therefore, performing the cleaning of both the measuring cleaning process and the post-measurement cleaning process provides the most desirable results in the TOC measurement.

A highly accurate desired measurement result is achieved only in a purification process during the measurement; however, a highly accurate continuous measurement is not achieved by the post-measurement cleaning process alone.

EMBODIMENTS

Although the effectiveness of the present invention will be described with reference to examples, the present invention is not limited to these examples and it goes without saying that various design changes are possible within the scope of the present invention.

A common condition in the embodiment is as shown in [Table 1].

TABLE 1

| COMMON CONDITION | |
|---|---|
| combustion pipe | φ22 × 200 |
| test water volume | 5.6 ml |
| simultaneous washing and testing water | 3 times |

TABLE 1-continued

| COMMON CONDITION | |
|---|---|
| combustion furnace | 500 W |
| drying time | 15 minutes |
| burning time | 40 minutes |
| drying temperature | 200° C. |
| combustion temperature | 800° C. |
| carrier | 100 ml/min |
| cleaning | 0.5 seconds × 50 times every 5 seconds |

(Note)
Each measurement value is an average value of five measurements.
A blank value is an average value (0.023) obtained by measuring the pure water five consecutive times.
A theoretical value of $CO_2$ generation under the above condition is 100 mg/l -> 1.045 cc.

Example 1

Using the TOC meter described with reference to FIG. 1, under the common conditions illustrated in Table 1, by measuring a residual degree of the measurement with and without the "cleaning process during measurement" by the following operation procedure, a cleaning effectiveness of the present invention will be clarified. The "cleaning process after measurement" is not performed.

(1) TOC Measurement without "Cleaning Process During Measurement"

The TOC measurement (without "cleaning process during measurement") is carried out by the following procedure using sample water having an organic matter concentration of 100 mg/l as the test water.

Figure 4A:
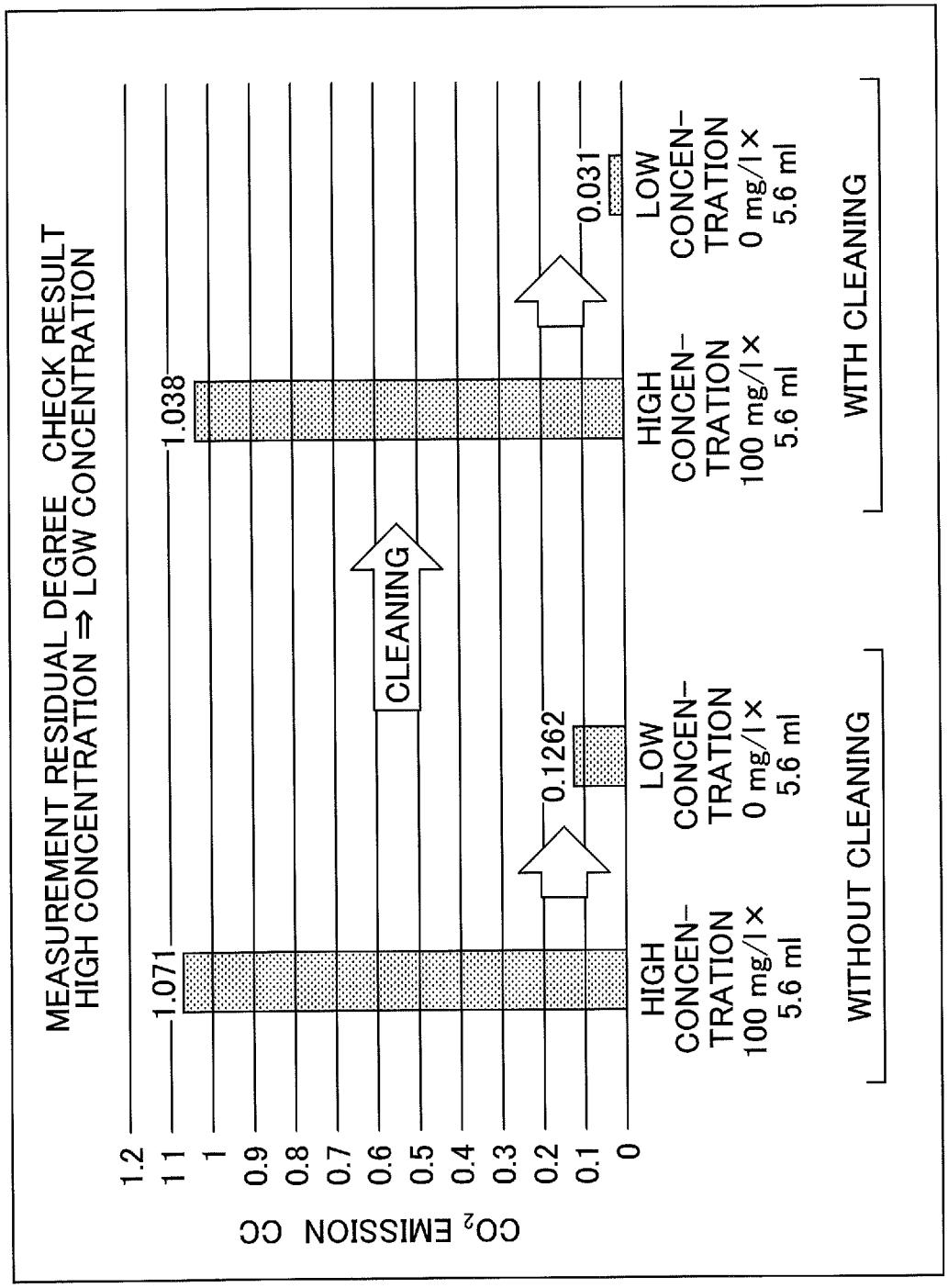
FIG. 4A, FIG. 4B, and FIG. 4C are diagrams illustrating results of checking a measurement residual degree of the TOC measurement apparatus of the present invention.

1) Test Water Injection Process for Injecting to Combustion Tube=>2) Carrier Air Generation Process=>3) Drying Process of Test Water in Combustion Tube (drying time 15 minutes)=>4) Burning Process (burning time 40 minutes) =>7) Measurement of Combustion Gas Concentration A result is illustrated in FIG. 4A.

Next, in order to investigate an influence of measurement residues in the above-described test water (organic matter concentration: 100 mg/l) by the TOC measurement (without "cleaning process during the measurement"), this TOC meter was continuously used, a specified amount (5.6 ml) of the pure water (organic substance concentration: 0 mg/l) was used as the test water, and the TOC measurement was carried out by the same operation procedure as described above (in a case of not conducting "cleaning process during measurement"). The result is illustrated in FIG. 4A.

(2) TOC Measurement with "Cleaning Process During Measurement"

The TOC measurement (with "cleaning process during measurement") is carried out by the following procedure using sample water having an organic matter concentration of 100 mg/l as the test water.

1) Test Water Injection Process for Injecting to Combustion Tube=>2) Production Process of Carrier Air=>3) Carrier Air Drying Process Of Test Water In The Combustion Tube (drying time: 15 minutes)=>4) Burning Process (burning time: 40 minutes)=>5) Cleaning Process during Measurement=>7) Measurement of Combustion Gas Concentration A result is illustrated in FIG. 4A.

Next, in order to investigate the influence of measurement residues in the TOC measurement (with "cleaning process during measurement") of the above-described water test (organic matter concentration: 100 mg/l), this TOC meter was continuously used, a specified amount (5.6 ml) of the pure water (organic substance concentration: 0 mg/l) was used as the test water, and the TOC measurement was performed according to the same operation procedure as described above (a case of not conducting the "cleaning process during measurement").

The result is illustrated in FIG. 4A.

As can be seen from the result of in FIG. 4A, it can be confirmed that there is a large difference in the TOC measurement results between existence of the "cleaning process during measurement" and nonexistence of the "cleaning process during measurement".

As can be seen from the result of in FIG. 4A, it has been confirmed that there is a large difference in the measurement results of the TOC between the case of nonexistence of the "cleaning process during measurement" and the case of existence of the "cleaning process during measurement".

That is, in the case of existence of the "cleaning process during measurement", because the TOC measurement value of the test water having the organic matter concentration of 100 mg/l is 1.038 cc, is 1.015 cc by subtracting the blank value (0.023 cc), and this value corresponds to 97% of the theoretical $CO_2$ generation value, that is, 1.045 cc. Because the measurement with extremely high accuracy is conducted, it can be confirmed that the cleaning method during measurement according to the present invention is highly effective.

Furthermore, even in a case of using this TOC meter continuously and of using the specified amount (5.6 ml) of the pure water (organic matter concentration: 0 mg/l) as the test water, the measured value obtained by the TOC measurement with cleaning process during the measurement is 0.031, which is 0.008 cc higher than a blank value (0.023 cc). From this fact, little influence of residues (contamination) has appeared.

With respect to the above described case, in a case of nonexistence of the "cleaning process during measurement", the TOC measurement value of the test water with the organic matter concentration of 100 mg/l is 1.071 cc. When subtracting the blank value (0.023 cc), 1.048 cc is acquired and this value is more than the theoretical value of $CO_2$ generation: 1.045 cc, which is more than 0.003 cc. It is considered that the influence of residues (contamination) greatly appears due to the TOC measurement being performed without the "cleaning process during measurement". Furthermore, the TOC meter was continuously used, a specified amount (5.6 ml) of the pure water (organic substance concentration: 0 mg/l) was used as a test water, and the TOC measurement was carried out without the "cleaning process during measurement", so as to obtain a measured value. From the fact that the measured value is larger than the blank value (0.023 cc) by more than 0.1032 cc, it is understood that the influence of the residue (contamination) also appears.

Example 2

The TOC meter described in FIG. 1 was used, two measurements with and without the "cleaning process during measurement" were conducted in accordance with the same operation procedure as that in Example 1, and a measurement residual degree was confirmed, so as to clarify cleaning effectiveness of the present invention. The TOC measurement was carried out in accordance with a procedure, in which first, a measurement was carried out using pure water having a organic matter concentration of 0 mg/l as the test water, and subsequently, the TOC meter was continuously used to perform the TOC measurement with the organic matter concentration of 100 mg/l as the test water. A result is illustrated in FIG. 4B.

Figure 4B:
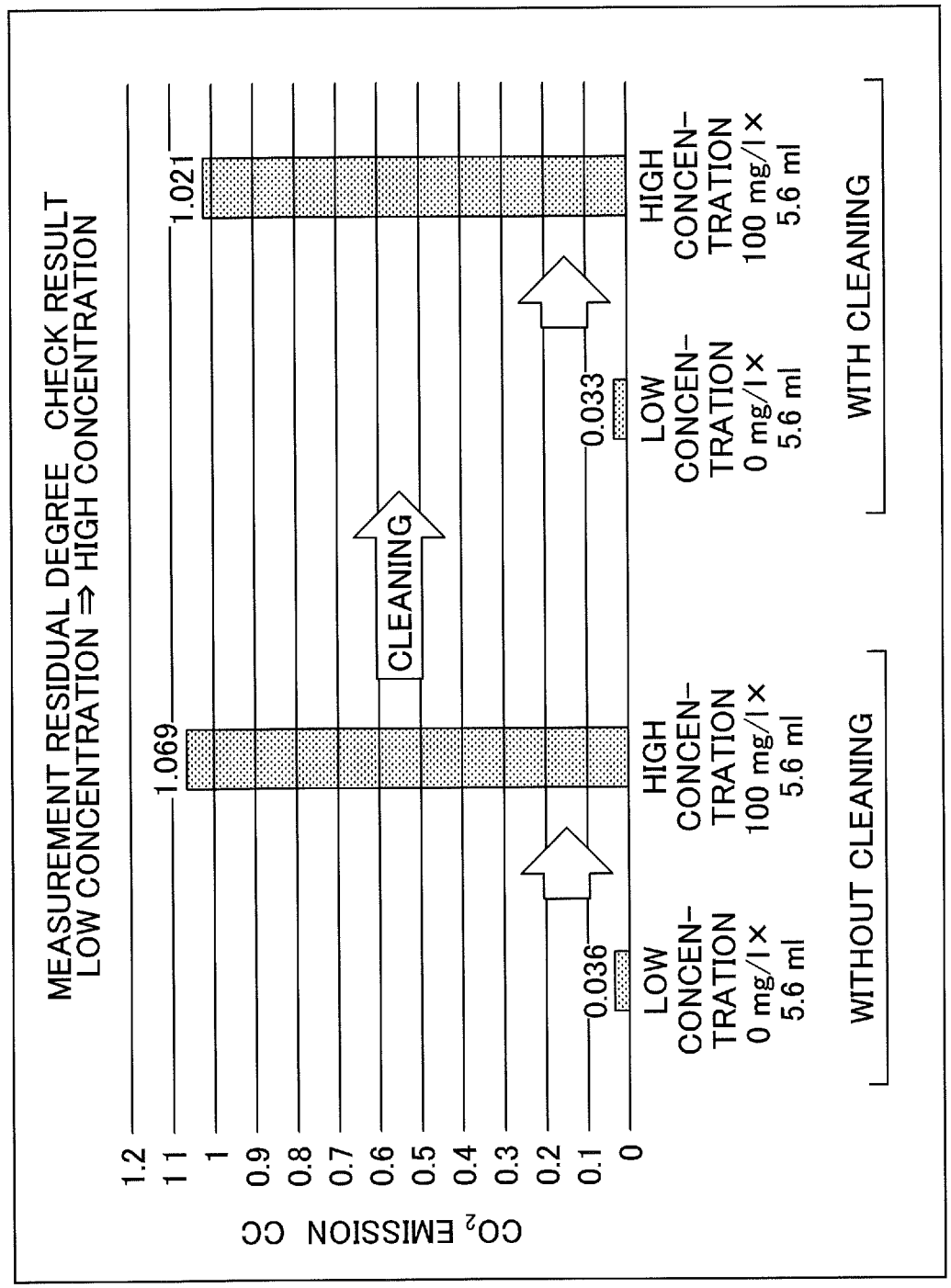

Referring to FIG. 4B, by performing the measurement with the pure water at first, it seems to be in the same state as a case of cleaning the TOC meter. However, unless performing cleaning operation, which is a technical feature of the present invention, namely, a cleaning operation of injecting pure water into the combustion tube 14 during the pure water being driven for inching at constant intervals for a specified number of times, as is apparent from the result illustrated in FIG. 4B, it can be confirmed that there is still a large difference in the TOC measurement result of the test water having the organic matter concentration of 100 mg/l, which is followed by the first measurement, with respect to cases of existence and nonexistence of the "cleaning process during measurement". That is, unburned residues are not removed unless a purification (cleaning) operation, which is a technical feature of the present invention, is carried out. Hence, it can be seen that the influence of residues (contamination) still remains in the TOC measurement result subsequently acquired.

Reference Example

The TOC meter described in FIG. 1 was used, two measurements with and without the "cleaning process during measurement" were conducted three times in accordance with the same operation procedure as that in Example 1. A result is illustrated in FIG. 4C.

Figure 4C:
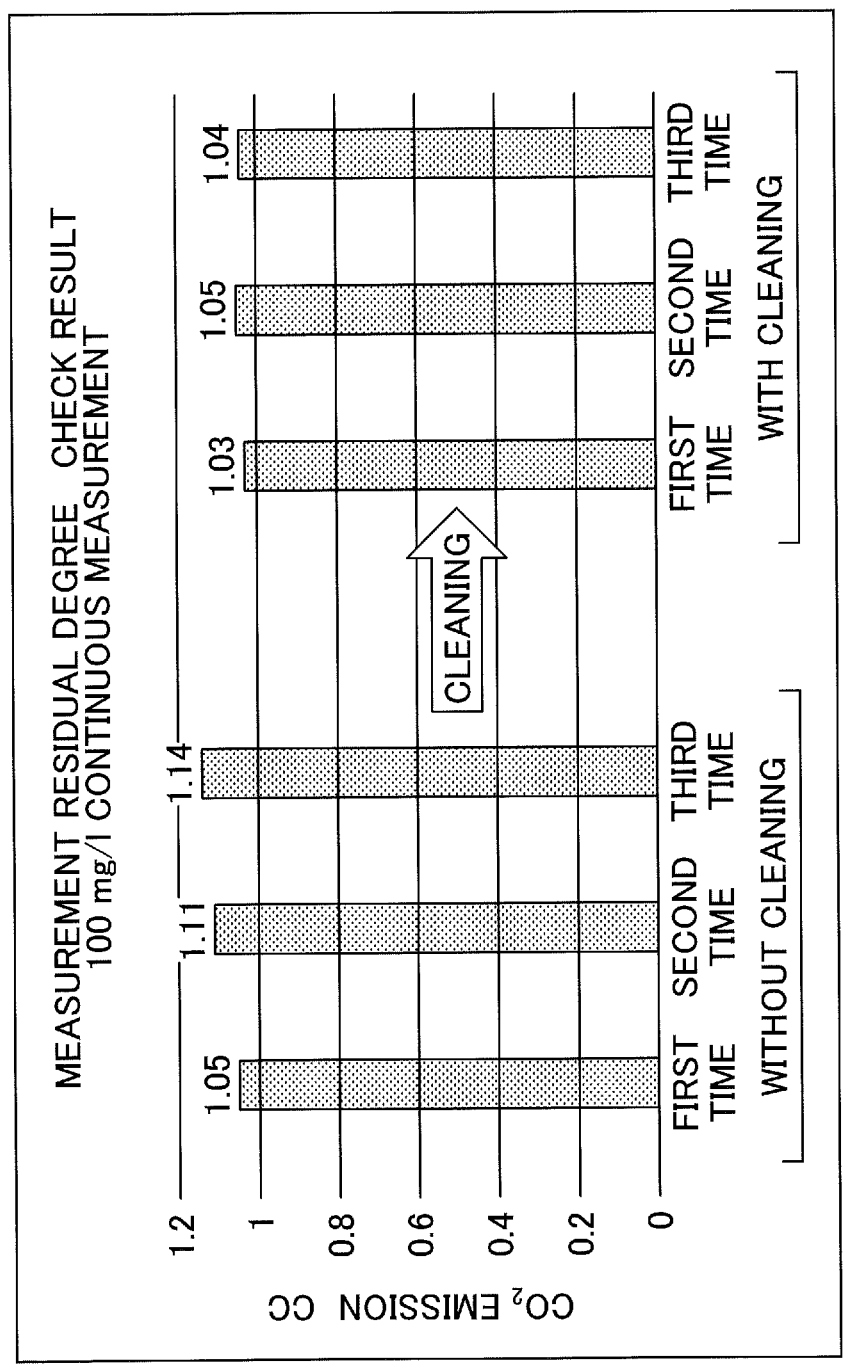
Figure 5:
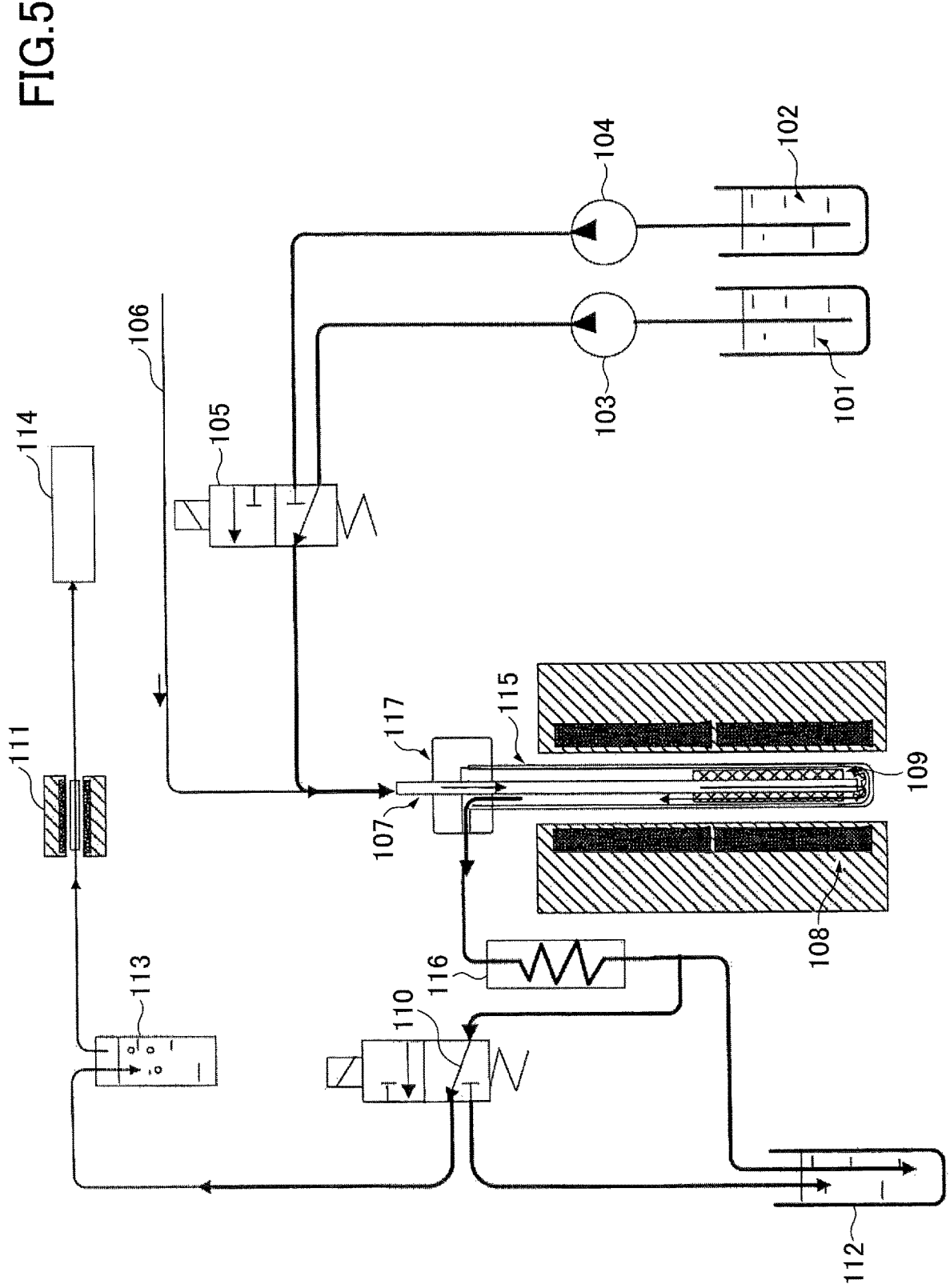
FIG. 5 is a diagram illustrating a basic TOP measurement apparatus in a related art.

As is apparent from the result illustrated in FIG. 4C, if a purification (cleaning) operation during the measurement, which is a technical feature of the present invention, that is, a purification (cleaning) operation during the measurement, in which pure water is riven for inching at regular intervals, for a specified number of times, and the pure water is injected into the combustion tube 14 in extremely small amounts, is conducted for each measurement, there is almost no fluctuation in three consecutive TOC measurement results of the test water with an organic matter concentration of 100 mg/l. That is, while a height difference of the measured value is extremely small (±0.01 with respect to an average value), in a case in which the purification (cleaning) operation during the measurement is not performed, three consecutive TOC measurement results of the test water with an organic matter concentration of 100 mg/l show large fluctuation, that is, a height difference among the measured values is extremely large (±0.05 with respect to the average value). Moreover, the fact that the TOC measured value is larger than a case in which the TOC measured value is measured during each measurement (0.06 larger than the average value) means that there is a measurement residual (contamination) as much as the TOC measured value is increased. By confirming the measurement residual degree, the effectiveness of the purification (cleaning) operation during the measurement of the present invention became clear.

The reason why a purification (cleaning) effect during measurement of the present invention is high is that steam at a high temperature close to 800° C. can be used instead of general steam cleaning (steam at approximately 100° C.).

According to the present invention, it is possible to realize a method for cleaning a combustion tube in a TOC measurement apparatus of the following (1) to (10), and particularly, it is possible to realize a method for measuring TOC, in which accurate and highly precise TOC measurement is achieved by cleaning a combustion tube, and a TOC measurement apparatus used for the same.

In a first aspect of a TOC measuring method, in an injecting process, test water is injected into a combustion tube. In a drying process, the combustion tube is controlled to be 120° C. to 250° C. by heating the combustion tube in a state of flowing carrier air in accordance with a generation process that generates the carrier air by discharging stored water filled in a combustion gas storage tank 29 or the carrier air storage tank 38, so that steam generated in the drying process is discharged outside the combustion tube to be cooled and removed. In heating and burning processes, after completion of the drying process, temperature is increased in the combustion tube to be 600° C. to 850° C., and the dried organic carbon is heated and burned. Combustion gas is generated and guided to the combustion gas storage tank. In a purification process, an inside of the combustion tube is purified due to high pressure steam generated by injecting pure water into the combustion tube with an extremely small amount at constant intervals at a plurality of times, when the burning process is substantially finished and temperature inside the combustion tube is controlled to be 600° C. to 850° C. The burning process ends when organic carbon removed in the purification process is burned and oxidized. In a cooling process, the combustion tube is cooled. In a measurement process, either one of a first measurement manner and a second measurement manner is conducted. The first measurement manner guides the generated combustion gas to the combustion gas storage tank by the carrier air and pushes out a total combustion gas stored in the combustion gas storage tank into an infrared meter so as to measure a carbon dioxide gas concentration of the combustion gas. The second measurement manner guides the generated combustion gas to the infrared meter by the carrier air so as to measure the carbon dioxide gas concentration of the combustion gas.

In a second aspect of the TOC measuring method, when the temperature inside the combustion tube reaches 300° C. to 600° C. in the cooling process of the combustion tube, a process may be further conducted to inject pure water into the combustion tube with an extremely small amount at regular intervals at a plurality of times, so as to further purify the combustion tube.

In a third aspect of the TOC measuring method, the extremely small amount of the pure water may be 0.1 to 0.6 ml/time.

In a fourth aspect of the TOC measuring method, the plurality of times may correspond to 5 to 50 times.

In a fifth aspect of the TOC measuring method, the constant interval may be in a range from 5 to 20 seconds.

In a sixth aspect of the TOC measuring method, a process may be conducted to forcibly peel off organic carbon scattered and adhered in a combustion tube by injecting pure water with a very small amount into the combustion tube at constant intervals at a plurality of times to generate high pressure steam, so as to purify the combustion tube, when a burning process during a TOC measurement is approximately finished and the temperature inside the combustion tube is controlled to be 650° C. to 850° C.

In a seventh aspect of the TOC measuring method, when temperature inside the combustion tube reaches 300° C. to 600° C. in a cooling process of the combustion tube, a process may be conducted to inject the pure water into the combustion tube at the constant intervals at the plurality of times, so as to further purify the combustion tube.

In an eighth aspect of a TOC measurement apparatus, a combustion section is formed by a combustion tube concentrically containing a test water injection tube, and a combustion tube heating furnace has a structure, in which a main heater 58 is laid concentrically on the outside of the combustion tube. A combustion tube input/output block 57 is provided in a protruding portion of the combustion tube. The protruding portion is not surrounded by the combustion tube heating furnace. In the combustion tube input/output block 57, a test water and/or carrier air supply section for supplying test water and/or carrier air and a pure water supply section for supplying pure water are provided so as to be supplied to the test water injection tube in a switchable manner. A combustion gas discharge port is provided and a steam trap section for recovering steam discharged from the combustion gas discharge port is connected and deployed to the combustion gas discharge port. An infrared meter measures the combustion gas other than the steam discharged from the combustion gas discharge port, in which the steam trap section is connected to the infrared meter. A gas storage section includes a gas storage tank, which is laid between the steam trap section and the infrared meter or which is laid in front of a carrier air supply section for supplying the carrier air.

In a ninth aspect of the TOC measurement apparatus, in a test water supply section, an inorganic carbon remover may be installed to remove inorganic carbons in test water.

In a tenth aspect of the TOC measurement apparatus, an auxiliary combustion tube may be deployed between the steam trap section and the gas storage section or between the steam trap section and the infrared meter.

In the TOC measuring method of test water according to the present invention, particularly, in the TOC measuring method for carrying out a process for cleaning a combustion tube, during the TOC measurement, that is, when the burning process during the TOC measurement is approximately finished and the temperature in the combustion tube reaches 600° C. to 850° C., preferably 700° C. to 850° C., by injecting pure water (also called "zero water") into the combustion tube, high pressure steam is generated, so unburned organic carbon scattering and adhering to the combustion tube is forcibly peeled off and cleaned (referred to as "cleaning during measurement").

Moreover, in addition to the cleaning process during the measurement, at a time when the temperature inside the combustion tube reaches 300° C. to 600° C., preferably 400° C. to 500° C. in the cooling process after completion of combustion, a process for injecting pure water into the combustion tube to generate high pressure steam in order to clean the inside of the combustion tube (hereinafter, referred to as "post-measurement purification process"), whereby achieving further sufficient cleaning of the inside of the combustion tube. Therefore, as in the related arts, there is no cleaning with poor efficiency due to low temperature steam or no workload for disassembling and cleaning the combustion tube each time the measurement is completed. That is, it becomes possible to easily and efficiently clean the inside of the combustion tube without taking much time and labor.

Further, in cleaning during the measurement in the TOC measurement method of the present invention, washing water injected into the combustion tube at 650° C. to 850° C. generates high pressure steam, and the unburned organic carbon scattering and adhering to the inside of the combustion tube is forcibly separated and burned by this steam. That is, similar to a normal combustion, the generated combustion gas is measured and recorded by the infrared meter after the gas is stored, and thus, it is possible to realize measurement with higher precision and higher accuracy (it is confirmed that a recovery rate with respect to the theoretical value of $CO_2$ generation is 95% or more).

Accordingly, even if the cleaning is performed during the measurement, an initial purpose can be sufficiently attained. In the post-measurement cleaning process, in which the measurement is performed in addition to purification during the measurement, that is, pure water is injected into the combustion tube at 300° C. to 600° C. in the cooling process, in which the combustion has ended, the injected pure water similarly generates high pressure steam. By this high pressure steam, it is possible to further clean the combustion section, and to prevent residual contamination.

A method for cleaning a combustion tube in the TOC measuring method for test water according to the present invention is simple and is concluded by being carried out during the TOC measurement referred to as the "purification process during measurement" and/or the "post-measurement purification process". After the TOC measurement is completed, it is possible to continuously perform a next TOC measurement and to minimize the influence due to the contamination at the previous measurement. It is possible to achieve a remarkable effect such an accurate and highly precise continuous measurement.

INDUSTRIAL APPLICABILITY

The present invention does not require workload of disassembling and washing the combustion tube 14 every measurement end. During the measurement, that is, in the latter half of the burning process, at the time when the combustion is almost finished, by injecting pure water into the combustion tube 14 for a specified number of times at regular intervals with a very small amount, it is possible to completely clean unburned TOC components scattered and adhered to the combustion tube 14. That is, because the unburned TOC components are forcibly peeled off and burned, it is possible to extremely simply and easily perform a continuous TOC measurement with high precision. Therefore, not only improving the measurement efficiency and measurement accuracy of the TOC measurement but also improving labor saving, the present invention significantly contributes to a development of all industrial fields requiring the TOC measurement.

The present international application claims priority based on Japanese Patent Application No. 2018-067105 filed Mar. 30, 2018, and entire contents of Japanese Patent Application No. 2018-067105 are herein incorporated by reference for the present international application.

What is claimed is:

1. A method for measuring total organic carbon (TOC) in test water, comprising:
   an injecting process that injects test water into a combustion tube;
   a drying process that controls the combustion tube to be 120° C. to 250° C. by heating the combustion tube in a state of flowing carrier air in accordance with a generation process that generates the carrier air by discharging stored water filled in a combustion gas storage tank or a carrier air storage tank, so that steam generated in the drying process is discharged outside the combustion tube to be cooled and removed;
   heating and burning processes, after completion of the drying process, that increase temperature in the combustion tube to be 650° C. to 850° C., and that heat and burn dried organic carbon, in which combustion gas is generated and guided to the combustion gas storage tank;
   a purification process that purifies an inside of the combustion tube due to high pressure steam generated by injecting pure water into the combustion tube with an extremely small amount at constant intervals at a plurality of times, when the burning process is substantially finished and temperature inside the combustion tube is controlled to be 650° C. to 850° C., wherein the burning process ends when organic carbon removed in the purification process is burned and oxidized;
   a cooling process that cools the combustion tube; and
   a measurement process that conducts either one of a first measurement manner and a second measurement manner, the first measurement manner guiding the generated combustion gas to the combustion gas storage tank by the carrier air and pushing out a total combustion gas stored in the combustion gas storage tank into an infrared meter so as to measure a carbon dioxide gas concentration of the combustion gas, the second measurement manner guiding the generated combustion gas to the infrared meter by the carrier air so as to measure the carbon dioxide gas concentration of the combustion gas.

2. The method as claimed in claim 1, further comprising a process that injects pure water into the combustion tube with an extremely small amount at regular intervals at a plurality of times, so as to further purify the combustion tube, when the temperature inside the combustion tube reaches 300° C. to 600° C. in the cooling process of the combustion tube.

3. The method as claimed in claim 1, wherein the extremely small amount of the pure water is 0.1 to 0.6 ml/time.

4. The method as claimed in claim 1, wherein the plurality of times correspond to 5 to 80 times.

5. The method as claimed in claim 1, wherein the constant interval is in a range from 5 to 20 seconds.

6. A method for measuring total organic carbon (TOC) in test water, comprising:
   a process that forcibly peels off organic carbon scattered and adhered in a combustion tube by injecting pure water with a very small amount into the combustion tube at constant intervals at a plurality of times to generate high pressure steam, so as to purify the combustion tube, when a burning process during a TOC measurement is approximately finished and the temperature inside the combustion tube is controlled to be 650° C. to 850° C.

7. The method as claimed in claim 6, further comprising a process that injects the pure water into the combustion tube at the constant intervals at the plurality of times, so as to further purify the combustion tube, when temperature inside the combustion tube reaches 300° C. to 600° C. in a cooling process of the combustion tube.

* * * * *